United States Patent [19]

Iritani et al.

[11] 4,247,539

[45] Jan. 27, 1981

[54] **HEMAGGLUTININ OF *HAEMOPHILUS GALLINARUM***

[76] Inventors: Yoshikazu Iritani, 151, Manjojiki-cho, Okamedani, Fukakusa, Fushimi-ku, Kyoto-shi, Kyto Pref.; Ken Katagiri, 5-1-25, Satsukigaoka, Ikeda-shi, Osaka Pref.; Hitoshi Arita, 1-5-4, Suimeidai, Kawanishi-shi, Hyogo Pref., all of Japan; Jun'ichi Kawanami, deceased, late of Kawanishi, Japan; by Emiko Kawanami, heir, 4-11-10, Daiwahigashi, Kawanishi-shi, Hyogo Pref., Japan; Akira Kawanami, heir, 4-11-10, Daiwahigashi, Kawanishi-shi, Hyogo Pref., Japan; Mariko Kawanami, heir, 4-11-10, Daiwahigashi, Kawanishi-shi, Hyogo Pref., Japan

[21] Appl. No.: 14,158

[22] Filed: Feb. 22, 1979

[30] Foreign Application Priority Data

Feb. 22, 1978 [JP] Japan ................................. 53-20021

[51] Int. Cl.$^2$ ..................... A61K 39/02; A61K 39/40
[52] U.S. Cl. ......................................... 424/92; 424/87
[58] Field of Search ................................... 424/92, 87

[56] References Cited

PUBLICATIONS

Iritani, Y., Katagiri, K., Tsuji, K., Avian Dis. 22 (4), 793–797 (1978), Slide–Agglutination Test of *Haemophilus Gallinarum* Antigen Treated by Trypsin to Inhibit Spontaneous Agglutination.

Iritani, Y., Hidaka, S., Avian Dis. 20 (3): 614–616(1976), Enhancement of Hemagglutinating Activity of *Haemophilus Gallinarum* by Trypsin.

Iritani, Y., Sugimori, G., Katagiri, K., Avian Dis. 21 (1): 1–8 (1977), Serologic Response to *Haemophilus Gallinarum* in Artificially Infected and Vaccinated Chickens.

Iritani, Y., Hidaka, S., Katagiri, K., Avian Dis. 21 (1), 39–49 (1977), Production and Properties of Haemoglutinin of *Haemophilus Gallinarum*.

Iritani, Y., Iwaki, S., Katagiri, K. J. Comp. Pathol. 88 (3): 395–399 (1978), Production of Extra Cellular Antigen in Culture Supernate by *Haemophilus Gallinarum*.

*Primary Examiner*—Shep K. Rose
*Attorney, Agent, or Firm*—Wenderoth, Lind & Ponack

[57] ABSTRACT

Hemagglutinin of *Haemophilus gallinarum* which is obtained by treating cells of *Haemophilus gallinarum* with trypsin and is useful for prevention and treatment of infectious coryza.

1 Claim, 1 Drawing Figure

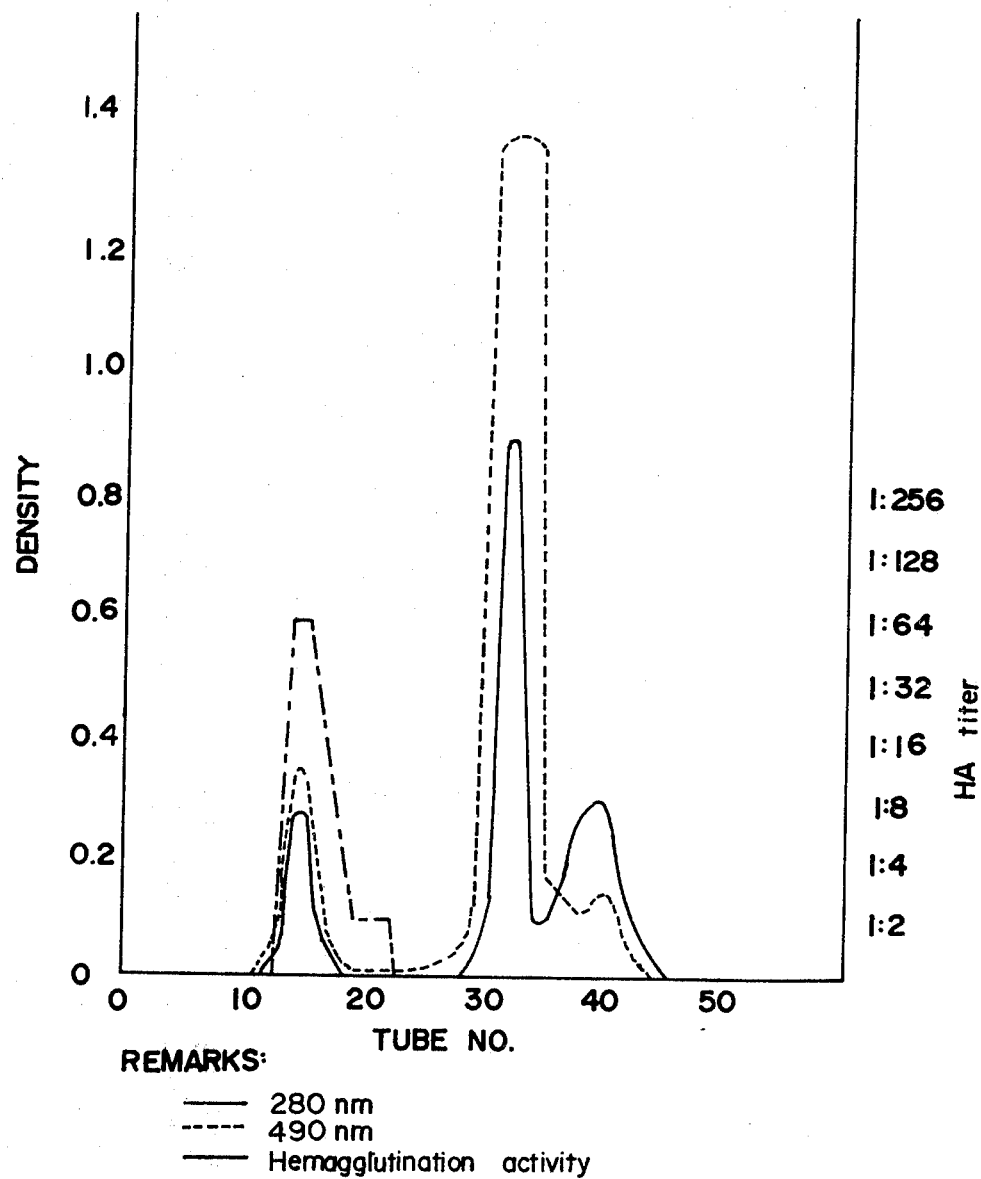

HEMAGGLUTININ OF *HAEMOPHILUS GALLINARUM*

This invention relates to a hemagglutinin of *Haemophilus gallinarum* and the production thereof. Further, it relates to a method for prevention and treatment of infectious coryza, infection caused by *Haemophilus gallinarum*.

There are many vaccines on the market to prevent infectious coryza of chickens caused by *Haemophilus gallinarum* (hereinafter called HG). These vaccines, however, bring on necrosis (Matsumoto and Yamamoto: Avian Dis. 15, 109–117 (1971)) or hematoma (Chiba et al.: The Abstract of the 79th Meeting of Japan Veterinary Medical Association (1975)). It has been reported that a purified endotoxin of HG is lethal to chicken embryo (Konno and Nakase: Japan. J. Bacteriolo. 32, 212 (1977)). Thus, solution of these adverse side-effects and creation of a highly safe new vaccine are strongly desired.

Meanwhile, it has been known that hemagglutination inhibition (hereinafter called HI) antibodies increase if HG vaccine is inoculated into chickens, and the chickens with high HI titers can resist infection (Otsuki and Iritani: Avian Dis., 18, 297–304 (1974)). Nagasawa et al. reported that indirect hemagglutinin was obtained by ultrasonication of HG cells and that it appeared to be a lipo-polysaccharide (The Abstract of the 83rd Meeting of Japan Veterinary Medical Association (1977)), but the details have not been reported.

The present inventors objective was to prepare a vaccine with high safety, and they have been studying hemagglutinin. It was found that hemagglutinin was one of the effective components of vaccines and could be isolated by treating HG with trypsin. The inventors have acertained that the novel hamagglutinin has antigenicity, and have completed this invention.

The process for preparing hemagglutinin comprises treating HG with trypsin. The details of the process are as follows:

The strain to be used is preferably selected from the strains which frequently infect chickens and have high antigenicity to make a vaccine with high protective effect. HG strain No. 221 (National Veterinary Assay laboratory, Ministry of Agriculture and Forestry, Japan) and strain No. 0083 (Department of Epidemiology & Preventive Medicine, School of Veterinary Medicine, University of California) are preferred because of the high antigenicity.

The fermentation is effected in the usual manner. Liquid media are preferable. They may be exemplified by Kato's broth, chicken meat infusion broth supplemented with chicken serum, brain heart infusion broth supplemented with β-diphosphopyridine nucleotide (DPN) and the like. The composition of Kato's broth is disclosed in Iritani and Hidaka; Avian Dis., 20, 614–616 (1976) and chicken meat infusion broth supplemented with chicken serum is disclosed in Otsuki and Iritani: Avian Dis., 18, 297–304 (1974). Brain heart infusion broth supplemented with DPN is disclosed in Yamamoto and Somersett: Avian Dis., 8, 441–453 (1964).

Cells in the cultured broth are collected by usual means, for example, centrifugation and the like. The centrifugation is effected at the temperature which is usually used. The cells are washed with and resuspended in a suitable buffer solution. The cell suspension in a desired concentration is treated with trypsin. The buffer for the washing and the suspension may be exemplified by buffered saline, phosphate buffered saline and the like.

Treatment with trypsin is effected in the following manner: Concentrated cells are suspended in a suitable buffer. The suspension is mixed with a solution of trypsin and the cells are sensitized. The sensitization is practised in a usual manner. Namely, the treatment may be effected at the optimum pH and at the optimum temperature of trypsin. Hemagglutination activity is checked during the treatment with trypsin and the treatment should be continued until release of hemagglutinin is recognized. Finally digestion of trypsin is inhibited by adding trypsin-inhibitor.

The HG cells may be pretreated with neuraminidase, as occasion demands, before the treatment with trypsin. The pretreatment will facilitate release of hemagglutinin. The treatment with neuraminidase is effected on HG cells in a buffer solution. A suspension of HG cells is mixed with a buffer solution of neuraminidase and the cells are sensitized. The sensitization is carried out in a usual manner, i.e. at the optimum pH and at the optimum temperature of neuraminidase.

After treatement with trypsin, the suspension of cells may be centrifuged and the supernatant is further purified by usual methods such as membrane filtration, gel filtration, electrophoresis, ultracentrifugation and the like to give purified hemagglutinin. The hemaglutinin of this invention has antigenicity to chicken infectious coryza.

The physicochemical properties of the hemagglutinin are as follows:

(1) the molecular weight of the subunit is about 39,000 (measured by SDS-polyacrylamide gel electrophoresis (SDS-Page method)).

(2) protein is filamentous in structure, (3) eluted at or near the $V_o$ value of Sepharose 6B, (4) loss of the antigenicity and hemagglutination activity by heating at 100° C. for 5 minutes.

(5) maintenance of the hemagglutination activity by heating at 70° C. for less than 5 minutes.

(6) constituent amino acids (and their ratio): lysine (0.73), histidine (0.22), arginine (0.31), aspartic acid (1.00), threonine (0.53), serine (1.09), glutamic acid (1.20), glycine (2.30), alanine (1.02), valine (0.71), isoleucine (0.37), leucine (0.68), tyrosine (0.18), phenylalanine (0.31). The hemagglutinin with the above properties is novel.

The present invention will now be further illustrated and described by way of the following specific example.

EXAMPLE

HG strain No. 221 is cultured in Kato's broth at 37° C. for 48 hours.

The cultured cells are collected by continuous-flow centrifugation at 10,000 rpm at 2°–5° C. at a flow rate of 3.6 liters per hour and washed twice with 2 M saline. Phosphate buffered saline (hereinafter called PBS) is added thereto to make the final concentration 200 times the concentration of the initial cultured broth. The cells are incubated at 37° C. overnight and then washed twice with PBS. The washed cells are adjusted with PBS to be 400 times the concentration of the initial cultured broth. Neuraminidase is dissolved in PBS at a ratio of 1 mg per 1 ml. The solution is added to an equal volume of the cell suspension. The cells are incubated at 37° C. for 30 minutes and then washed with PBS by centrifugation at 12,000×g at 2–5° C. for 30 minutes.

Thus-obtained cells are resuspended in an equal volume of PBS. The suspension (1 liter) is mixed with 0.25% trypsin solution in PBS (1 liter) prepared from crystal trypsin (Bovine Pancrease, PL Biochemical Co., & Ltd.) and sensitized at 37° C. for 30 minutes.

The suspension is centrifuged at 30,500×g at 2°-5° C. for 30 minutes. To the supernatant (1 liter) is added 0.25% solution of trypsin inhibitor in PBS (1 liter) to prevent the further digestion of trypsin. Cell-free hemagglutinin (hereinafter called HA) is obtained from the supernatant.

Two lines are found in HA by immunodiffusion test with HG-infected serum. The solution of HA is concentrated to 30 to 50 times by membrane filtration (Millipore, 25,000 MW) and centrifuged at 30,500×g at 2°-5° C. for 30 minutes. The supernatant is fractionated by gel filtration with Sepharose 6B and eluted with 0.1 M Tris-hydrochloric acid buffered saline (pH 7.8). Protein is followed by the absorbance of ultra-violet spectrum at 280 nm and sugar is by the phenol-sulfuric acid method (490 mn). The hemagglutination activity is also measured by the method described in Iritani and Hidaka: Avian Dis., 20, 614–616 (1976). The tubes containing 0.2 ml of diluted hemagglutinin solution and 0.5% suspension of erythrocytes (0.2 ml) are placed at room temperature for 30 to 45 minutes. The titer value was read at the most diluted concentration showing hemagglutination activity. Three peaks appear by the tracings with protein and suger (see attached drawing). The first peak has hemagglutination activity. The fractions of the first peak having hemagglutination activity results in a single precipitation line by immunodiffusion test with the serum of chicken hyper-immunized with the fractions. A purified HA (hereinafter called PHA) can be identified with the line. A single line is shown when the fraction having hemagglutination activity is tested by immunodiffusion with the HG-infected chicken serum.

The hemagglutinin is observed in filamentous structure by electron-microscope.

The following experiments have been conducted to clarify the properties of the hemagglutinin.

EXPERIMENT 1

Release of cell-free hemagglutinin (HA) by treatment with trypsin (1) Method: After treatment with neuraminidase the Example, the cell suspension was centrifuged to give a supernatant and a sediment containing the neuraminidase-sensitized cells. The cell suspension treated with trypsin was also centrifuged to give a supernatant and a sediment containing the trypsinized cells. Trypsin-inhibitor was added to the latter supernatant. The procedures of treatment with trypsin and centrifugation were repeated on to the latter sediment.

The hemagglutination titer was measured for all these supernatants and sediments in the same manner as in the Example.

(2) Results: The results are shown in Table 1.

TABLE 1

| | Hemagglutination Titer | | | | | |
|---|---|---|---|---|---|---|
| Experiment No. | 1 | | 2 | | 3 | |
| Preparation | Sed.* | Sup.** | Sed. | Sup. | Sed. | Sup. |
| Initial Cell | 128 | | 32 | | 64 | |
| After treatment with Neuraminidase | 256 | <1 | 16 | <1 | 64 | <1 |
| After Trypsinization | | | | | | |
| First | 256 | 16 | 128 | 32 | 64 | 8 |
| Second | 1042 | 8 | 128 | 8 | 256 | 8 |
| Third | 256 | 8 | 128 | 4 | 128 | 1 |

Notes:
*Sed. = Sediment
**Sup. = Supernatant

As shown above, cell-free hemagglutinin is released to the supernatant by treating cells of HG with trypsin.

EXPERIMENT 2

Measurement of molecular weight of hemagglutinin (1) Method: A lyophilized sample of purified hemagglutinin (PHA) was washed three times with PBS by ultracentrifugation at 54,000×g at 2°–5° C. for 30 minutes and hemagglutination activity was checked. Both hemagglutinin preparations before and after the washing were subjected to SDS-polyacrylamide-gel electrophoresis.

(2) Results: The PHA preparation before the washing showed several protein bands but that after the washing showed a single band which was identified with the main band of the former preparation. The molecular weight of the band calculated from the electrophoretic mobility is 39,000. The band was not affected by 2-mercaptoethanol.

EXPERIMENT 3

Cross hemagglutination inhibition (HI) test (1) Method: The chicken serum immunized with PHA was measured for the HI titer with HG cells and PHA. The measurement is described in Otsuki and Iritani: Avian Dis., 18, 297–304 (1974) in detail. Each diluted serum (0.2 ml) was mixed with an equal volume of solution of HG cells and PHA (4 units per 0.2 ml). The mixture was left to standing at room temperature for 10 minutes and then 0.5% suspension of erythrocytes (0.4 ml) was added thereto. The mixture was left standing at room temperature for 30 to 40 minutes. HI titer was read at the maximum dilution of serum which inhibited hemagglutination completely.

(2) Results: The HI titer of the chicken serum immunized with PHA was 10 both with HG cells and PHA. HI titer of the chicken serum immunized with HG cells was also measured with HG cells and PHA. Both the HI titers were 256. Non-immunized serum showed the HI titer of less than 2.5 with HG cells and PHA. It is concluded from the results that no serological difference exists between HG cells and PHA.

EXPERIMENT 4

Effect of heat on PHA (1) Method: The preparations of PHA were heated at 100° C., 70° C., and 60° C. for 5 minutes and at 56° C. for 30 minutes, respectively. These preparations were measured for the hemagglutination titer with one kept at room temperature for 60 minutes and another stored in a refrigerator, which was used as control. The measurement was effected in the same manner as in the Example.

(2) Results: The results are shown in Table 2.

TABLE 2

| Temperature (°C.) | Heating time (min.) | Hemagglutination titer |
|---|---|---|
| 100 | 5 | <2 |
| 70 | 5 | 16 |
| 60 | 5 | 16 |
| 56 | 30 | 16 |
| Room Temp. | 60 | 16 |
| Control | — | 16 |

It is obvious from Table 2 that the Hemagglutination titer of PHA remarkably dropped by heating at 100° C. for 5 minutes, but not by heating at lower than 70° C.

EXPERIMENT 5

Immunization of chickens with PHA (1) Method: Five white Leghorn chickens, 30 days old, were inoculated three times with PHA (1 ml) with adjuvant (aluminium hydroxide gel) every two weeks and challenged with HG three weeks after the last inoculation. A preparation of PHA heated at 100° C. for 5 minutes was inoculated in the same manner. The chickens were observed for respiratory symptoms and lesions. Hemagglutination titer in serum was also measured. The isolation of HG was checked in the necropsied chickens. The measurement of HI titer was practised in the same manner as in Experiment 3.

(2) Results: The results are shown in Table 3.

TABLE 3

| Immunization | Geometric mean HI titer | | A | B | C |
| | Before Challenge | After Challenge | | | |
|---|---|---|---|---|---|
| with PHA | 12.6 | 13.4 | 0/5* | 0/5* | 0/5* |
| with heated PHA | 5 | 5 | 5/5 | 5/5 | 5/5 |
| No immunization | 5 | 5 | 5/5 | 5/5 | 5/5 |

Notes:
*Number of positive chickens /Number of tested chickens
A = Respiratory sympton
B = Lesion at necropsy
C = Recovery of HG Table 3 shows that the chickens inoculated with PHA have raised HI titers. Neither appearance of respiratory symptom nor lesion was observed on the chickens inoculated with PHA. No HG was detected in those chickens. Moreover, caeseous deposit, necrosis and hematoma in the pectoral muscle of chickens inoculated with PHA were not observed in the local side. The HI titer did not remarkably change after the challenge. The immunization with heated PHA did not raise the HI titer. All of the chickens immunized with heated PHA fell sick and HG was isolated from the chickens. The same results were observed in non-immunized chickens. It is obvious from the above experiments that the hemagglutinin of HG can be effectively used for preparing a preventive vaccine for chicken infectious coryza. It is also applicable to produce therapeutic antibody or antiserum.

Some embodiments using the present hemagglutinin of HG are shown as follows:

(1